United States Patent [19]
Dreckmann-Behrendt

[11] Patent Number: 5,914,336
[45] Date of Patent: Jun. 22, 1999

[54] METHOD OF CONTROLLING THE SERUM SOLUBILITY OF ORALLY ADMINISTERED TORASEMIDE AND COMPOSITION RELATING THERETO

[75] Inventor: Bruno Dreckmann-Behrendt, Mannheim, Germany

[73] Assignee: Boehringer Mannheim GmbH, Mannheim, Germany

[21] Appl. No.: 09/089,067

[22] Filed: Jun. 2, 1998

[51] Int. Cl.$^6$ .................................................... A61K 31/44
[52] U.S. Cl. ........................................... 514/347; 514/869
[58] Field of Search ..................................... 514/347, 869

[56] References Cited

U.S. PATENT DOCUMENTS

Re. 34,580   4/1994   Topfmeier et al. ..................... 546/291
Re. 34,672   7/1994   Topfmeier et al. ..................... 514/347

*Primary Examiner*—Kimberly Jordan
*Attorney, Agent, or Firm*—Nikaido, Marmelstein, Murray & Oram LLP

[57] ABSTRACT

A method of controlling the serum solubility of orally administered torasemide is disclosed. A new crystallin modification of torasemide, called modification III which has significantly higher rates of solubilization than the known crystallin form of torasemide, modification I, is blended with amounts of modification I to produce a preselected level of torasemide in serum at a given time following administration. Compositions containing amounts of modification I and modification III, sufficient to achieve the desired serum levels of torasemide, are also disclosed.

13 Claims, 6 Drawing Sheets

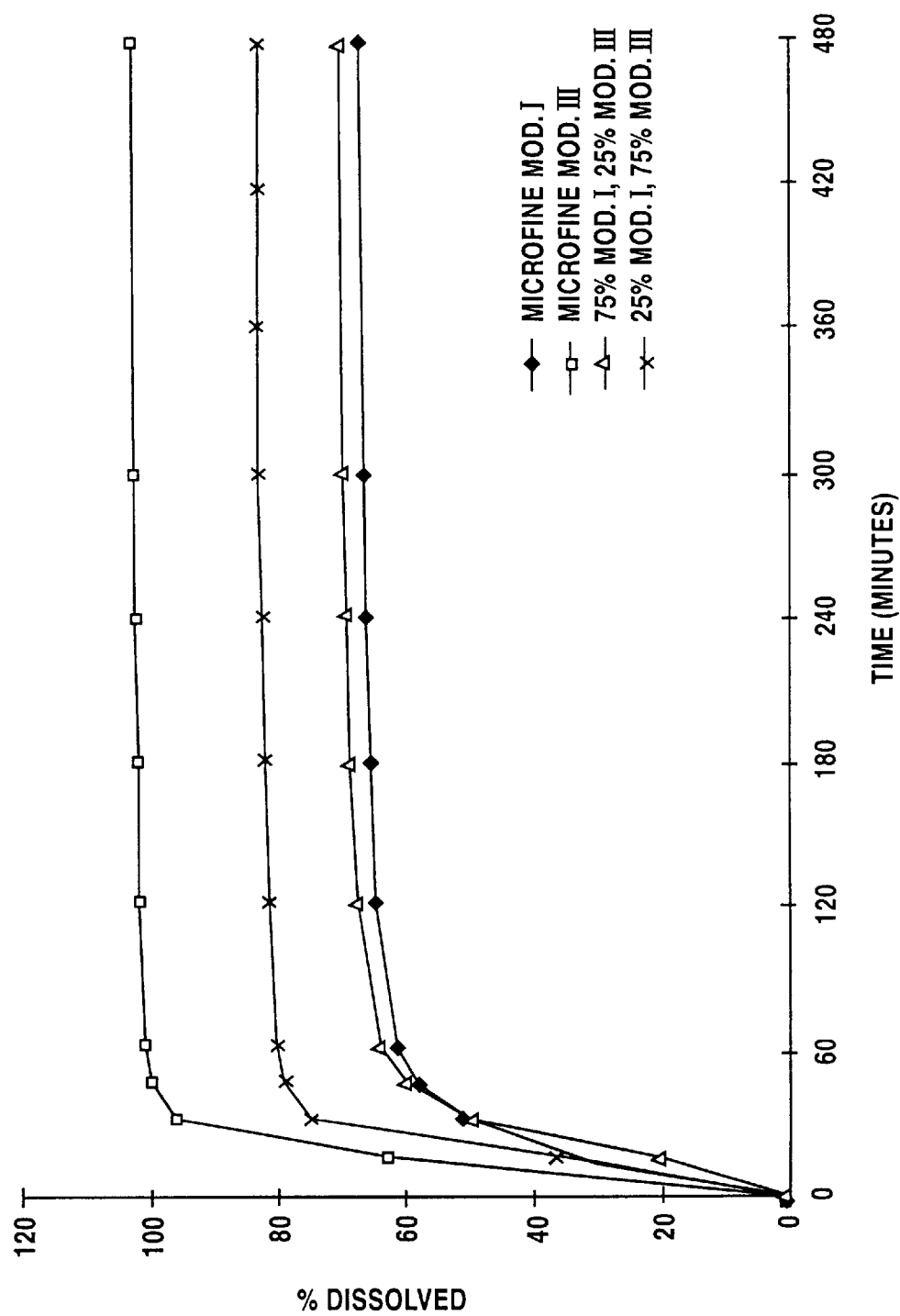

METHOD OF CONTROLLING THE SERUM SOLUBILITY OF ORALLY ADMINISTERED TORASEMIDE AND COMPOSITION RELATING THERETO

BACKGROUND OF THE INVENTION

Torasemide is a known compound which has been approved by the U.S. Food and Drug Administration for use as a diuretic.

Torasemide (1-isopropyl-3-[(4-m-toluidino-3pyridyl)-sulphonyl)-urea) is a compound with interesting pharmacological properties which is described in Example 71 of U.S. Pat. No. Re 30,633 as 3-isopropylcarbarmylsulfonamido-4-(3'-methyl)-phenylaminopyridine. In particular, this compound belongs to the class of loop diuretics as it blocks the sodium-potassium-2 chloride transport mechanism in the ascending limb of the loop of Henle. In contrast to other standard loop diuretics, however, it shows a less intense initial diuresis and a sustained duration of action.

In the preparation of torasemide, a purification is normally included in which the compound in question is dissolved in an aqueous or aqueous alcoholic solution of sodium hydrogen carbonate and, after filtering off from impurities, the torasemide is again precipitated out with an inorganic acid. In the case of this process, the product is obtained in the form of white crystals with a melting point of 163°–164° C. U.S. Pat. No. Re 30,633 does not mention any particular crystalline form of torasemide.

From Acta Cryst. 1978, pp. 2659–2662 and Acta Cryst., 1978, pp. 130.4–1310, it is known that torasemide can occur in two modifications each having a different X-ray crystallograph. Both modifications are simultaneously present when a solution of torasemide in petroleum ether/ethanol is slowly evaporated. The crystals, which are characterized not only as prisms with a melting point of 159–161.5° C. but also as leaflets with a melting point of 157.5–160° C., are, however, only described in these literature references with regard to their X-ray crystallographic properties. The modification with the melting point of 159–161.5° C., which is hereinafter referred to as modification I, crystallizes monoclinically in the space group $P2_1/c$ and has a true density of about 1.36, and the modification with the melting point of 157.5–160° C., which is hereinafter referred to as modification II, crystallizes monoclinically in the space group $P2/n$ and has a true density of 1.285.

The modification obtained in the case of the preparation and normal purification by precipitating the torasemide from an aqueous solution is modification II which usually also results in the case of recrystallisations from other solvents. Since this form, in the case of storage of the pure active material, does not change and, in the case of all purification experiments, forms the predominant form, it was assumed that this modification II was stable.

U.S. Reissue Pat. Nos. 34,672 and 34,580 are based on the discovery that torasemide of modification II, when it is present in very finely divided form in pharmaceutical tablets, rearranges more or less quickly into modification I, whereby the crystal size and speed of dissolving of the active material upon introducing the tablets into water can be significantly changed. Since, as was known, the speed of dissolving represents one of the important characteristics of a pharmaceutical form of administration and thus, in order to be able to dose reproducibly, must not differ from one tablet to another, the problem existed of finding a form of administration of torasemide which does not change its speed of dissolving during storage. Since the uncontrollable change of the speed of dissolving depends upon the rearrangement of modification II into modification I of the torasemide, it was obvious ab initio to use modification I.

From investigations it was found that modification I is stable in tablets and did not rearrange again back into modification II.

The applicant has recently discovered that a third form of torasemide exists, and has labelled this third form as modification III. Modification III is stable, and has significantly greater solubility than modification I above pH 3 and especially at a pH of approximately 7.4. Modification III is especially suitable for use as a diuretic where a rapid onset of diuretic effect is desired, or as a way to avoid IV therapy, since oral administration could be used.

SUMMARY OF THE INVENTION

The present invention is directed to a method of controlling the rate of solubilization of torasemide in serum after oral administration by blending amounts of modification III with amounts of modification I and/or II such as to produce the desired rate of solubilization lying between that of modification I and/or II and that of modification III. It is especially preferred to utilize a blend of modification I and modification III to produce that desired rate of solubilization lying between that of modification I and that of modification III.

The present invention is also directed to compositions comprising blends of modification I and modification III.

DESCRIPTION OF THE DRAWINGS

The invention will be understood more clearly with reference to the accompanying drawings, wherein

FIG. 6 is a plot similar to that of FIG. 5, but in water.

DETAILED DESCRIPTION OF THE INVENTION

Figure 1:
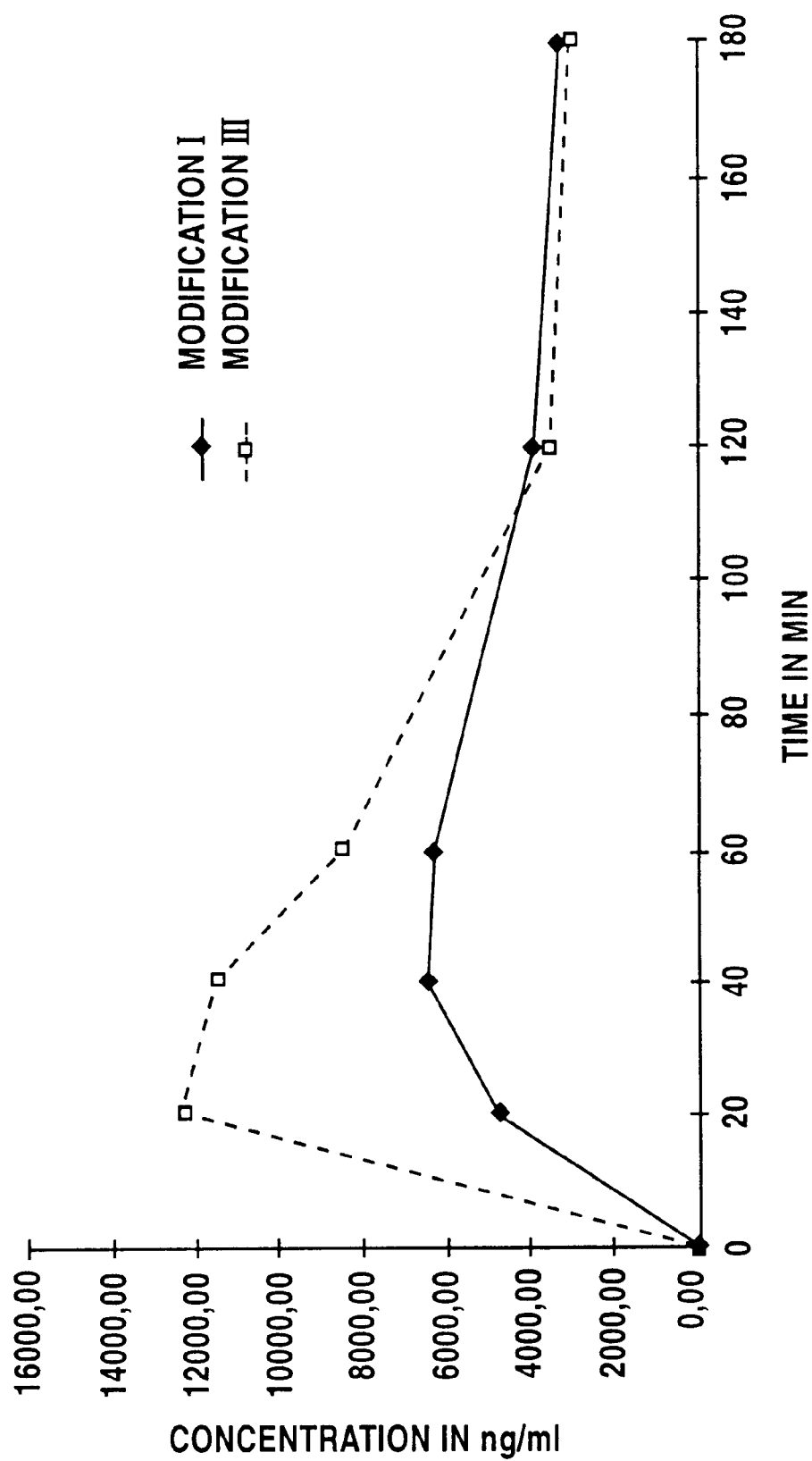
FIG. 1 is a plot of serum concentration levels in male rats of torasemide of modification I and modification III versus time after oral administration.
Figure 2:
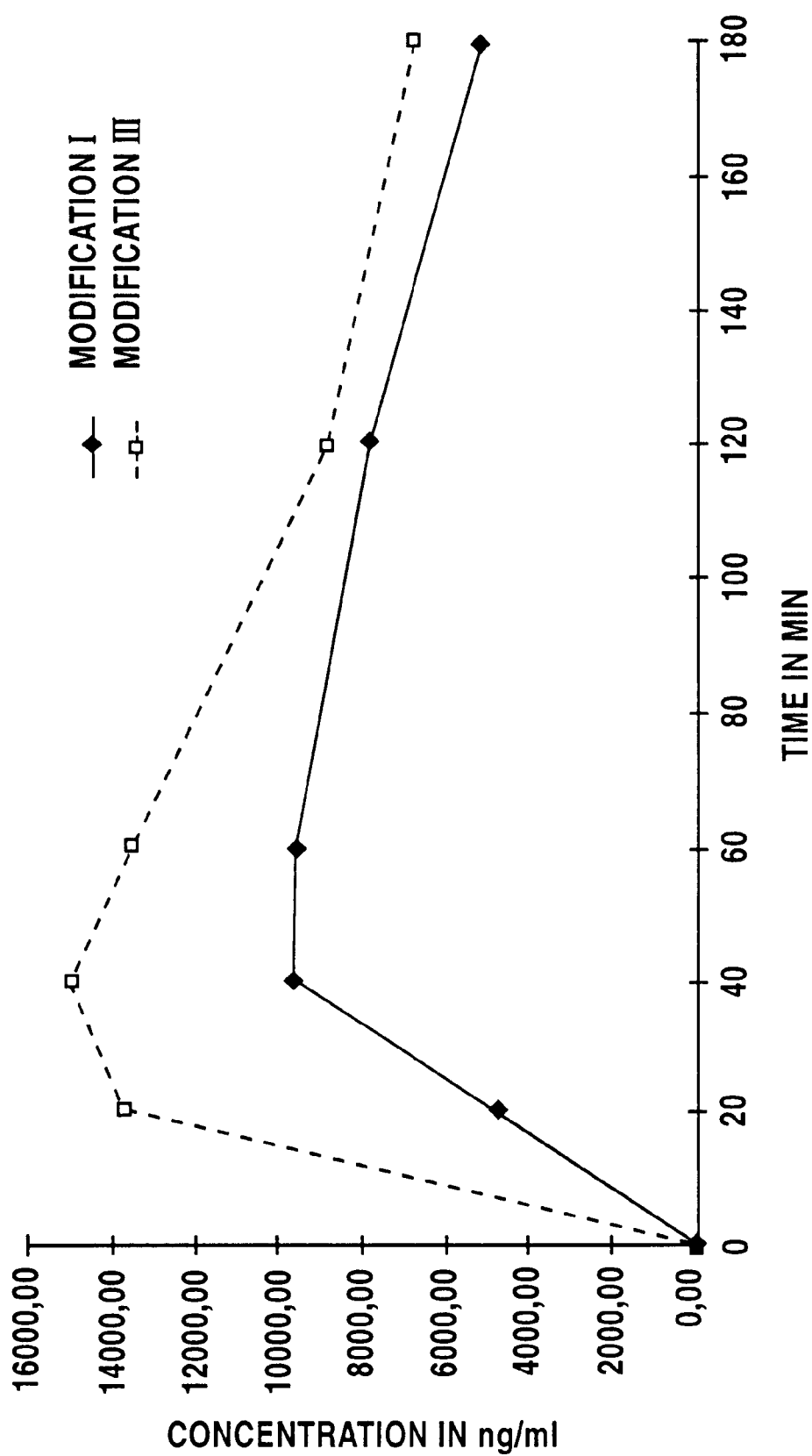
FIG. 2 is similar to FIG. 1, but reflects the serum concentrations in female rats.

The rate of solubilization of orally administered torasemide in the serum of a patient is controlled by blending amounts of modification III, which results in a significantly increased rate of solubilization in serum, with amounts of modification I such as to produce the desired rate of solubilization lying between that of modification I and that of modification III. Amounts of modification II can be added to the blend of the other modifications if desired, but there is no advantage in doing so, and normally the use of modification II will be considered undesirable, since modification II is relatively unstable. If modification II is used in such blends, it is best to use the resulting blends containing modification II shortly after unit dose tablets have been prepared, so as to maintain the desired rate of solubilization of the torasemide blend. If modification II is present in the blend, it is preferable that it be present in an amount of no more than about 30% by weight of the blend.

Relevant data of the two most important crystal forms (modification I and III) of torasemide are summarized in Table 1.

TABLE 1

Characteristic physico-chemical properties of Mod. I and Mod. III of Torasemide

|  | Mod. I | Mod. III |
|---|---|---|
| Habit | prismatic platelets | aggregates |
| Melting point (°C.)   Thermomicroscopy | 158–161 | 155–158 |
| DSC | 161.5[1] | 157.0[1] |
| Heat of fusion (kJ mol$^{-1}$) ± 95%-c.i. | 37.2 ± 1.9[1] | 29.9 ± 0.9[1] |
| Heat of transition (kJ mol$^{-1}$) at about 159° C. ± 95%-c.i. |  | −8.2 ± 2.1[2] |
| Heat of solution (kJ mol$^{-1}$) in I-butanol at 20° C. | 36.1 | 29.8 |
| First IR-Peak (cm$^{-1}$) | 3353 | 3356 |
| Water content (%) after storing in relative humidity of 92% at 25° C. | 0.2 | 1.2 (depending on particle size |
| Solubility (mmol L$^{-1}$) at 20° C. at pH 4.90 | 0.34 | 0.93 |
| True density (g cm$^{-3}$) ± 95%-c.i. | 1.363 ± 0.001 | 1.302 ± 0.009 |

[1]heating rate 5K min$^{-1}$
[2]the difference of the heats of fusion

Normally the blend will contain at least 20% by weight of modification I and at least 20% by weight of modification III (i.e., the weight ratio will be 20:80 to 80:20, although lesser amounts of either modification can be used when it is desired to fine tune the solubilization rate at a point near that of either pure modification I or pure modification III. Preferably the modification I and modification III will be used in a weight ratio of 30:70 to 70:30, more preferably from 40:60 to 60:40. By using such blends, the rate of solubilization and the peak concentration of torasemide can be controlled.

Torasemide of modification III can be characterized by a melting point of 155 to 158° C. (thermomicroscopy) and a true density of 1.302±0.009 g cm$^{-3}$ (versus 1.363±0.001 g cm$^{3}$ for modification I). In a preferred embodiment, the torasemide of modification III added to the blend is pure. This term "pure" means that the torasemide contains less than about 1% of modification I and/or II, and in any event less than amounts of modification I which adversely effect the stability of modification III.

Another aspect of the present invention is instant release pharmaceutical compositions containing the torasemide blends described herein. Oral forms of administration containing the torasemide blends of this invention are produced in the usual way with the use of pharmacologically acceptable adjuvants, for example sugar, starch, starch derivatives, cellulose, cellulose derivatives, mold separation agents and anti-adhesion agents, as well as possibly flow regulation agents. In particular, in the case of the use of torasemide blends of the present invention, aqueous process steps, for example granulation, can be carried out. It is preferred that the oral administration forms of the blends of the present invention are tablets or capsules.

It is preferred that when the active material torasemide is used with the following particle size distribution:

at least 90%≦96 μm. and, at least 50%≦48 μm.

As illustrated in FIG. 1, 20 minutes after administration modification III has more than twice the serum concentration as modification I, and after 40 minutes has almost twice the serum concentration as modification I. This rapid appearance of modification III in the serum after oral administration, as compared to modification I, indicates that modification III is particularly suitable for blending with modification I to raise the serum concentration, shortly after administration to a patient, to a desired level.

Modification I consists of thin hexa- to octagonal platelets, which start to melt at 158° C. Simultaneously with the end of the melting process at 161° C. the forming of bubbles in the melt can be observed. The remaining crystals in the melt do not grow during cooling. Also, the melt remains amorphous after cooling. On reheating of the glassy melt softening occurs at about 120° C. but no crystallization is observed. During annealing the melt color turns to brownish.

Modification III consists of aggregates of tiny crystals. The melting process starts at 155° C. and ends at 158° C. The behavior of the melt is analogous to that of modification I.

The torasemide of modification III, like torasemide of modification I or II, is an effective diuretic. Torasemide of modification I has been approved under the brand name Demadex in the U.S. for indications which include essentially hypertension; oedema due to congestive heart failure; and hepatic, pulmonary and renal oedema, and the blends disclosed herein can be used for the same indications. For essential hypertension the torasemide blend will generally be administered orally to adults at a dosage level of active ingredient of about 2.5 mg to about 5 mg. The initial oral dosage for oedema is generally five milligrams of torasemide for an adult, but increasing step wise up to about 20 mg per day if necessary.

For intravenous injection, the adult dosage, including that of elderly patients for oedema due to congestive heart failure or of hepatic organ, will normally be about 10 mg per day i.v., and increasing up to about 20 mg daily if required. The maximum recommend dose is about 40 mg per day. For oedema of renal organ, the starting dose will normally be about 20 mg of torasemide daily i.v. up to a maximum of about 200 mgs of torasemide daily if required.

Broadly, the torasemide blends of the present invention will be administered to adult patients at a daily dosage of about 2 to about 200 mg per day, and preferably about 5 to about 25 mg per day.

EXAMPLES OF THE INVENTION

Torasemide of modification I was prepared in accordance with the procedure described in U.S. reissue Pat. No. 34,580, and torasemide of modification III was prepared in accordance with the commonly assigned application entitled Torasemide of Modification III filed by Dreckmann-Behrendt et al of even date herewith, Ser. No. 09/089,066, the disclosures of which are hereby incorporated by reference for such methods described therein.

Example 1

In this and the following examples, microfine torasemide of modification I and microfine torasemide of modification III were blended together.

A blend was prepared of 75 wt. % of modification III and 25 wt. % of modification I, and a similar blend was prepared of 25 wt. % of modification III and 75 wt. % of modification I. These blends were incorporated into capsules containing 150 mg of total torasemide, and pure modification I and pure modification III 150 mg. capsules were also prepared. The capsules were subjected to dissolution testing in water, and in a citrate buffer (pH 4.5), at 37° C. under stirring. Table 1 below reports the solubility testing in citrate buffer:

TABLE I

TEST DISSOLUTION (150 mg in capsule, 37° C., 150 rpm 500 ml Citrate buffer), % dissolved

| Minutes | Microfine Mod. I | Microfine Mod. III | 75% Mod. I, 25% Mod. III | 25% Mod. I, 75% Mod. III |
|---|---|---|---|---|
| 0 | 0 | 0 | 0 | 0 |
| 15 | 13,4 | 63,3 | 22 | 30,3 |
| 30 | 30,3 | 91 | 39 | 64 |
| 45 | 38,3 | 97,4 | 47,2 | 77 |
| 60 | 43,5 | 99,5 | 52,5 | 78,8 |
| 120 | 54,9 | 101 | 61,2 | 80,5 |
| 180 | 61 | 101,5 | 62,9 | 81,2 |
| 240 | 63,2 | 101,6 | 63,5 | 81,5 |
| 300 | 63,1 | 101,8 | 64 | 81,8 |
| 480 | 63,9 | 102,5 | 64,6 | 82,4 |

The same capsules were tested in water, with the results obtained being set forth in Table 2 below:

TABLE 2

TEST DISSOLUTION (150 mg in capsules, 37° C., 150 rpm 500 ml water), % dissolved

| Minutes | Microfine Mod. I | Microfine Mod. III | 75% Mod. I, 25% Mod. III | 25% Mod. I, 75% Mod. III |
|---|---|---|---|---|
| 0 | 0 | 0 | 0 | 0 |
| 15 | 30,6 | 62,8 | 20,2 | 36,6 |
| 30 | 51,3 | 96,6 | 49,8 | 75,2 |
| 45 | 58,5 | 100,4 | 60,1 | 79,3 |
| 60 | 61,6 | 101,3 | 64,6 | 80,6 |
| 120 | 64,9 | 102,1 | 67,6 | 81,9 |
| 180 | 65,9 | 102,5 | 68,7 | 82,5 |
| 240 | 66,3 | 102,8 | 69,4 | 83,1 |
| 300 | 66,8 | 102,2 | 69,9 | 83,5 |
| 480 | 67,3 | 103,3 | 70,1 | 84,1 |

The results of this example can be summarized in Table 3 below:

TABLE 3

| | Water | | Citrate, pH 4.5 | |
|---|---|---|---|---|
| | 8 hr solubility, % | % of Theoretical | 8 hr solubility, % | % of Theoretical |
| Modification III | 103.3 | | 102.5 | |
| Modification I | 67.3 | | 63.9 | |
| Mod III: Mod I 75:25 | 84.1 | 94.3% | 82.4 | 92.9% |
| Mod III: Mod I 25:75 | 70.1 | 76.3% | 64.9 | 73.6% |

Example 2

Example 1 was repeated, but using mixtures containing 60:40 and 40:60 ratios of modification III:modification I. The solubility test results in citrate buffer, pH 4.5, are reported in Table 4 below, and the solubility testing in water is reported in Table 5 below:

TABLE 4

TEST DISSOLUTION (150 mg in capsule, 37° C., 150 rpm 500 ml Citrate buffer), % dissolved

| Minutes | Microfine Mod. I | Microfine Mod. III | 60% Mod. I, 40% Mod. III | 40% Mod. I, 60% Mod. III |
|---|---|---|---|---|
| 0 | 0 | 0 | 0 | 0 |
| 15 | 13,4 | 63,3 | 22,1 | 29,9 |
| 30 | 30,3 | 91 | 42,5 | 57,3 |
| 45 | 38,3 | 97,4 | 51,7 | 65 |
| 60 | 43,5 | 99,5 | 58,2 | 67,3 |
| 120 | 54,9 | 101 | 64,6 | 68,9 |
| 180 | 61 | 101,5 | 65,5 | 69,4 |
| 240 | 63,2 | 101,6 | 66 | 69,8 |
| 300 | 63,1 | 101,8 | 66,4 | 70,2 |
| 480 | 63,9 | 102,5 | 67,1 | 70,9 |

TABLE 5

DISSOLUTION TEST (150 mg in capsules, 37° C., 150 rpm 500 ml water), % dissolved

| Minutes | Microfine Mod. I | Microfine Mod. III | 60% Mod. I, 40% Mod. III | 40% Mod. I, 60% Mod. III |
|---|---|---|---|---|
| 0 | 0 | 0 | 0 | 0 |
| 15 | 30,6 | 62,8 | 30,9 | 30,5 |
| 30 | 51,3 | 96,6 | 57,2 | 65,8 |
| 45 | 58,5 | 100,4 | 62,9 | 70,4 |
| 60 | 61,6 | 101,3 | 64,7 | 71,5 |
| 120 | 64,9 | 102,1 | 66,9 | 72,7 |
| 180 | 65,9 | 102,5 | 67,8 | 73,3 |
| 240 | 66,3 | 102,8 | 68,6 | 73,9 |
| 300 | 66,8 | 103,2 | 69,4 | 74,3 |
| 480 | 67,3 | 103,3 | 69,5 | 74,7 |

The results of this Example can be summarized in Table 6 below

TABLE 6

| | Water | | Citrate, pH 4.5 | |
|---|---|---|---|---|
| | 8 hr solubility, % | % of Theoretic | 8 hr solubility, % | % of Theoretic |
| Modification III | 103.3 | | 102.5 | |
| Modification I | 67.3 | | 63.9 | |
| Mod. III: Mod. I 60:40 | 74.7% | 68.9 | 70.9 | 87.1 |
| Mod. III: Mod. I 40:60 | 69.5 | 81.7 | 67.1 | 79.3 |

Figure 3:
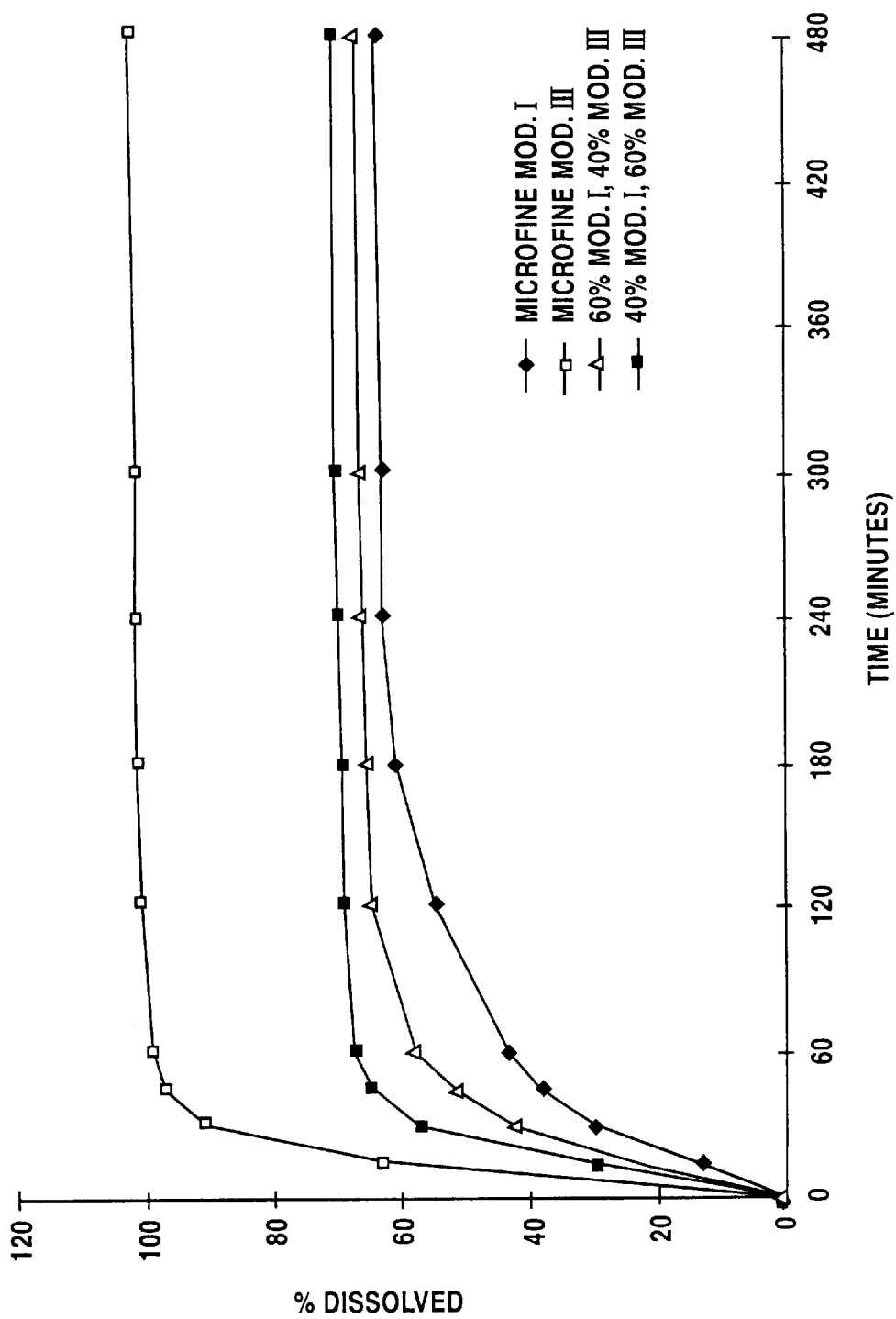
FIG. 3 is a plot of the in vitro dissolution rate in citrate buffer, pH 4.5, of capsules containing 150 mg of torasemide of modification III, torasemide of modification I, torasemide of a blend of 60% modification I and 40% of modification III, and torasemide of a blend of 40% modification I and 60% modification III, with the citrate buffer being maintained at 37° C. and being stirred by a stirrer revolving at 150 rpm.
Figure 4:
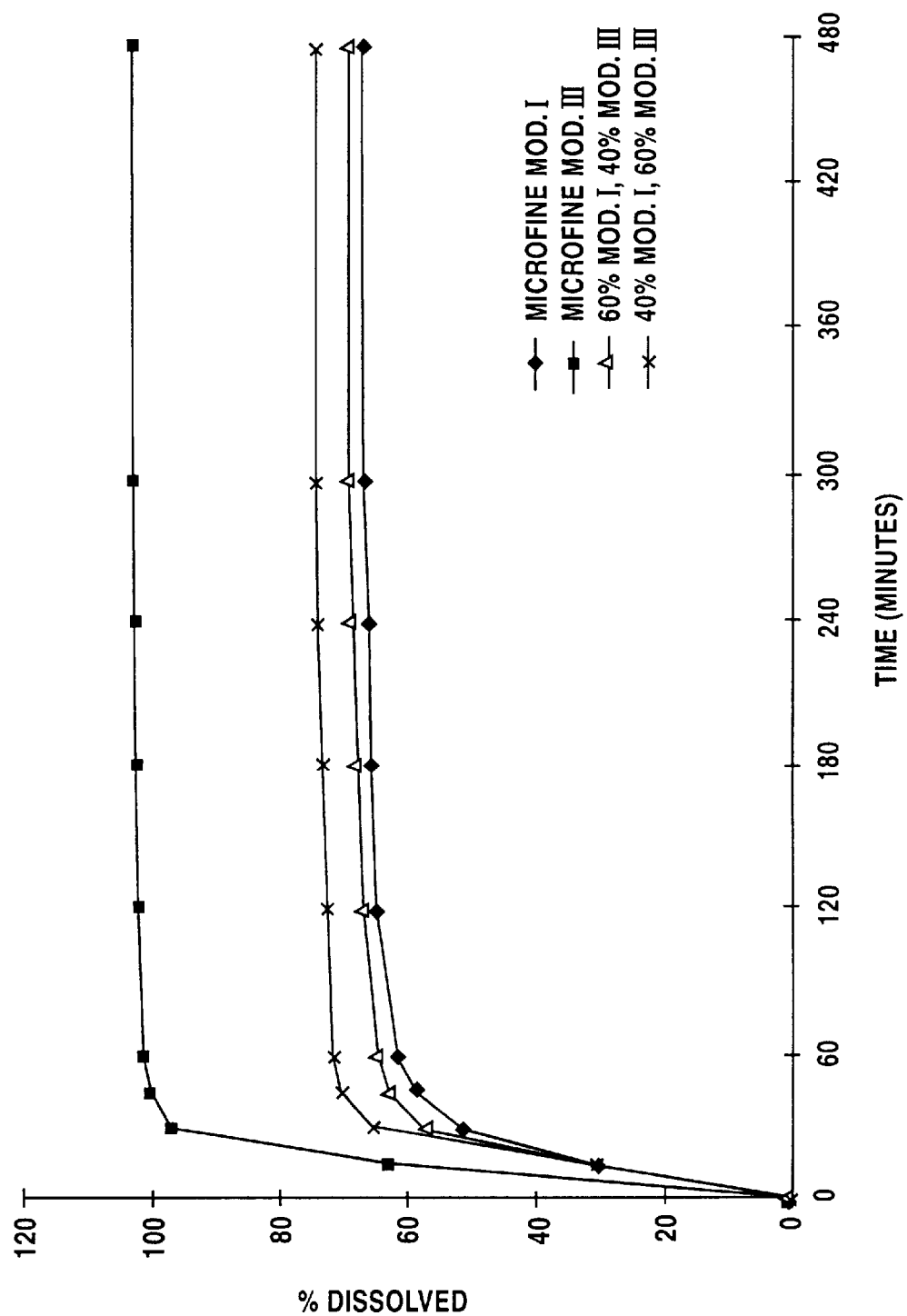
FIG. 4 is a plot similar to that of FIG. 3, but in water rather than citrate buffer.
Figure 5:
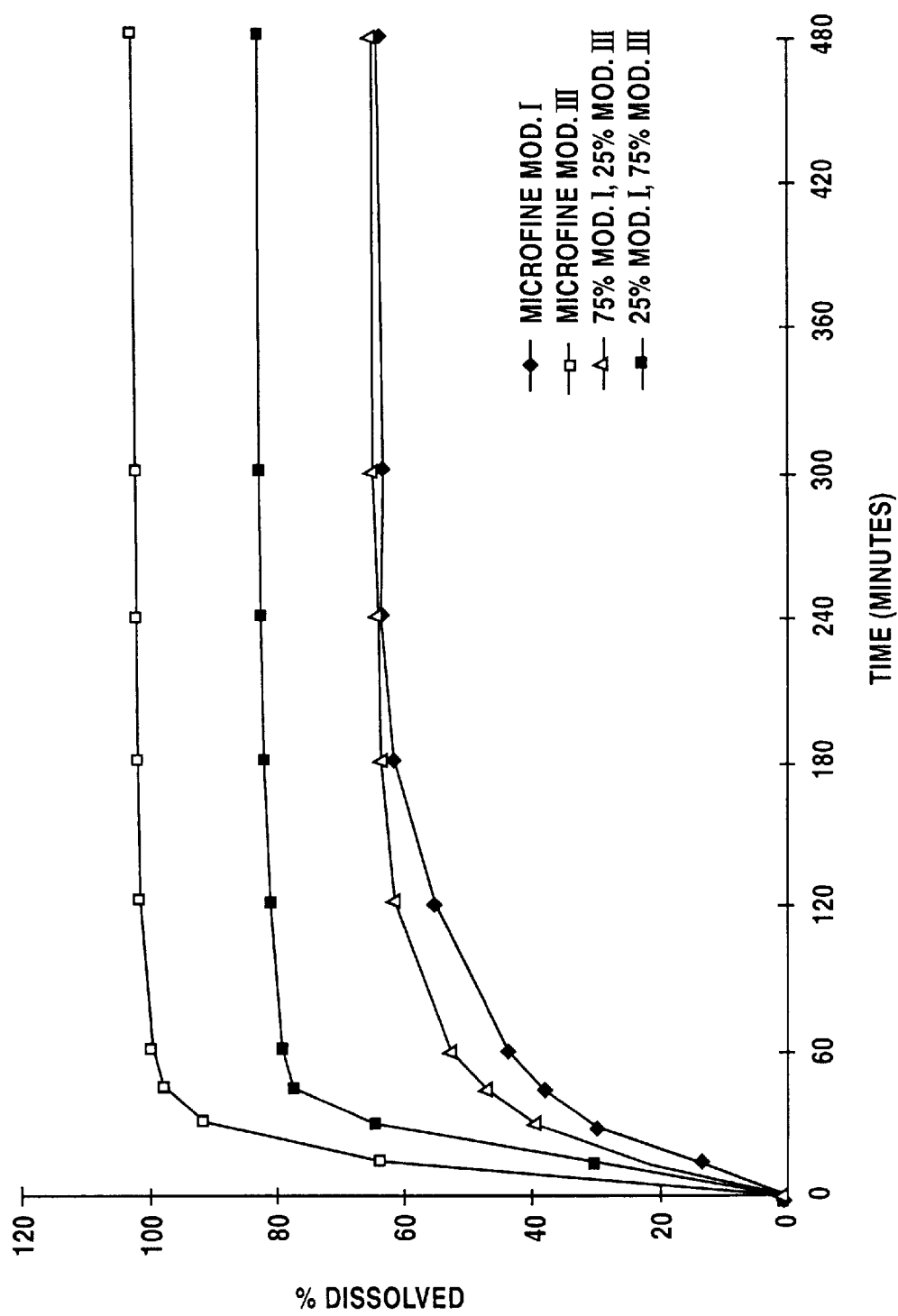
FIG. 5 is similar to FIG. 3, but the torasemide blends in the capsules contained 75% of modification I and 25% of modification III, and 25% of modification I and 75% of modification III.

The results reported in Table 1 above were plotted, and appear in the accompanying FIG. 5. The results set forth in Table 2 above were plotted and appear in the accompanying FIG. 6. The results set forth in table 4 were plotted and appear in the accompanying FIG. 3. The results set forth in Table 5 above were plotted and appear in the accompanying FIG. 4.

Example 3

A blend is prepared of 60 wt. % of modification III and 40 wt. % of modification I. The blend is tabletted using the procedure and formulation of Example 8 of the application filed herewith and identified above. The tablets are orally administered to patients, and after 20 minutes the concentration of torasemide in the serum of the patients is between that for pure modification III and that for pure modification I.

Example 4

Example 3 is repeated, except the blend of torasemide contains 40 wt. % of modification III and 60 wt. % of modification I. The concentration in the serum of patients after 20 minutes from administration is also between that of the two pure forms.

Example 5

Example 3 is repeated, except the blend of torasemide contains 45 wt. % of each of modifications I and III and 10 wt. % of modification II. The concentration after 20 minutes from administration to patients is between that for pure modification III and that for pure modification I.

I claim:

1. A method of controlling the rate of solubilization of torasemide in the serum of a patient in need of a diuretic, said method comprising
   a) selecting a desired rate of solubilization of torasemide,
   b) blending torasemide of modification I and modification III, wherein each modification is present in an amount of at least 20% by weight in an oral unit dose form and wherein the respective amounts are such as to produce the desired rate of solubilization, and
   c) orally administering the unit dose form containing the blend of modification I and modification III to said patient.

2. Method of claim 1, wherein the blend contains at least 40% by weight of modification III.

3. Method of claim 1, wherein the unit dose form in a tablet.

4. Method of claim 1, wherein the unit dose form is a capsule.

5. Method of claim 1, wherein the torasemide of modification III which is used in step b) is pure modification III.

6. An oral unit dose form of torasemide exhibiting a predetermined rate of solubilization of the torasemide in the serum of a patient receiving the torasemide by oral administration, the active ingredients of said unit dose form comprising at least 20% by weight of torasemide of modification III and at least 20% by weight of torasemide of modification I.

7. The unit dose form of claim 6, wherein the unit dose form is a tablet.

8. The unit dose form of claim 6, wherein the unit dose form is a capsule.

9. The unit dose form of claim 6, wherein said active ingredients comprise at least 40% by weight of modification III.

10. The unit dose form of claim 6 wherein the active ingredients also comprise torasemide of modification II in an amount of up to 30 weight %.

11. A torasemide blend comprising at least 20% by weight of torasemide of modification III and at least 20% by weight of torasemide of modification I.

12. The blend of claim 11, wherein the blend comprises at least 40% by weight of torasemide of modification III.

13. The blend of claim 11, wherein the blend also contains torasemide of modification II in an amount of up to 30% by weight.

* * * * *